(12) United States Patent
Takahashi

(10) Patent No.: US 10,323,005 B2
(45) Date of Patent: Jun. 18, 2019

(54) AROMATIC COMPOUND PRODUCTION METHOD

(71) Applicant: FUJIFILM Corporation, Tokyo (JP)

(72) Inventor: Motomasa Takahashi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/940,426

(22) Filed: Mar. 29, 2018

(65) Prior Publication Data

US 2018/0215716 A1   Aug. 2, 2018

Related U.S. Application Data

(63) Continuation of application No. PCT/JP2016/078783, filed on Sep. 29, 2016.

(30) Foreign Application Priority Data

Sep. 30, 2015 (JP) ................. 2015-193518
Sep. 7, 2016 (JP) ................. 2016-174539

(51) Int. Cl.
| | | |
|---|---|---|
| C07D 231/56 | (2006.01) | |
| B01J 31/02 | (2006.01) | |
| B01J 31/22 | (2006.01) | |

(52) U.S. Cl.
CPC ........ *C07D 231/56* (2013.01); *B01J 31/0202* (2013.01); *B01J 31/22* (2013.01); *B01J 31/2234* (2013.01); *B01J 31/2239* (2013.01); *B01J 2231/766* (2013.01); *B01J 2531/824* (2013.01)

(58) Field of Classification Search
CPC .................................. C07D 231/56
See application file for complete search history.

(56) References Cited

U.S. PATENT DOCUMENTS

| | | | |
|---|---|---|---|
| 5,132,447 A | 7/1992 | King, Jr. | |
| 6,031,105 A | 2/2000 | Wright | |
| 8,895,585 B2 | 11/2014 | Fujiwara et al. | |
| 9,051,310 B2 | 6/2015 | Fujiwara et al. | |
| 2008/0293972 A1 | 11/2008 | Gallou et al. | |
| 2011/0046394 A1 | 2/2011 | Ainge et al. | |

FOREIGN PATENT DOCUMENTS

| | | |
|---|---|---|
| GB | 934469 A | 8/1963 |
| JP | 48-21089 B1 | 6/1973 |
| JP | 4-221347 A | 8/1992 |
| JP | 10-139761 A | 5/1998 |
| JP | 2004-307412 A | 11/2004 |
| JP | 2004-307413 A | 11/2004 |
| JP | 2005-97303 A | 4/2005 |
| JP | 2009-514867 A | 4/2009 |
| JP | 2012-532186 A | 12/2012 |

OTHER PUBLICATIONS

Manjunatha et al (2014): Tetrahedron Letters vol. 55 (2014), 3348-3350.*
Wan Pyo Hong et al., "Pd-Catalyzed Semmler-Wolff Reactions for the Conversion of Substituted Cyclohexenone Oximes to Primary Anilines", Journal of the American Chemical Society, 2013, pp. 13664-13667, vol. 135, No. 37 (4 pages total).
Manjunatha Sulur et al., "Development of Scalable Manufacturing Routes to AZD1981. Application of the Semmler-Wolff Aromatisation for Synthesis of the Indole-4-amide Core", Organic Process Research & Development, 2012, pp. 1746-1753, vol. 16 (8 pages total).
Yves L. Janin et al., "A New Access to 1-Naphthylamines by an Equivalent Semmler-Wolff Reaction", Synthesis, Jan. 1993, pp. 57-59, No. 1 (4 pages total).
Kebiao Song et al., "Discovery and SAR study of 3-(tert-butyl)-4-hydroxyphenyl benzoate and benzamide derivatives as novel farnesoid X receptor (FXR) antagonists", Bioorganic & Medicinal Chemistry, Aug. 20, 2015, pp. 6427-6436, vol. 23, No. 19 (10 pages toatl).
Jan-E. Bäckvall et al., "Palladium-Hydroquinone Catalysed Electrochemical 1,4-Oxidation of Conjugated Dienes", Journal of the Chemical Society, Chemical Communications, 1987, pp. 1236-1238, No. 16 (4 pages total).
Sulur G. Manjunatha et al., "A novel synthetic approach to 4-acetamido-1-arylindazoles via Semmler-Wolff rearrangement of 1-aryl-6,7-dihydro-5H-indazol-4-one oxime", Tetrahedron Letters, 2014, pp. 3348-3350, vol. 55 (3 pages total).
International Search Report for PCT/JP2016/078783 dated Dec. 27, 2016 [PCT/ISA/210].
International Preliminary Report on Patentability with the translation of Written Opinion dated Apr. 3, 2018 issued by the International Bureau in PCT/JP2016/078783.

(Continued)

*Primary Examiner* — Golam M Shameem
(74) *Attorney, Agent, or Firm* — Sughrue Mion, PLLC

(57) ABSTRACT

Provided is a method for producing an aromatic compound, which can produce a particular aromatic compound at high yield and can be industrially utilized. According to the invention, there is provided a method for producing an aromatic compound, including an aromatization reaction which includes reacting an oxime compound represented by Formula (1) with an acylating agent in the presence of a hydroquinone compound and a palladium compound, and thus obtaining an aromatic compound.

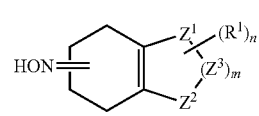

(1)

14 Claims, No Drawings

(56) References Cited

OTHER PUBLICATIONS

Office Action dated Sep. 11, 2018 from the Japanese Patent Office in counterpart Japanese Application No. 2016-174539.
Sulur G. Manjunatha et al., "A novel synthetic approach to 4-acetamido-1-arylindazoles via Semmler-Wolff rearrangement of 1-aryl-6,7-dihydro-5H-indazol-4-one oxime", Tetrahedron Letters, 2014, vol. 55, pp. 3348-3350 (total 3 pages).
Alok Kumar et al., "A hydroquinone based palladium catalyst for room temperature nitro reduction in water", RSC Advances, Aug. 2014, vol. 4, pp. 35233-35237 (total 6 pages).
Extended European Search Report dated Jun. 29, 2018 from the European Patent Office in counterpart European Application No. 16851720.9.

* cited by examiner

AROMATIC COMPOUND PRODUCTION METHOD

CROSS-REFERENCE TO RELATED APPLICATIONS

This application is a Continuation of PCT International Application No. PCT/JP2016/078783 filed on Sep. 29, 2016, which claims priorities under 35 U.S.C § 119(a) to Japanese Patent Application No. 2015-193518 filed on Sep. 30, 2015 and Japanese Patent Application No. 2016-174539 filed on Sep. 7, 2016. Each of the above application(s) is hereby expressly incorporated by reference, in its entirety, into the present application.

BACKGROUND OF THE INVENTION

1. Field of the Invention

The present invention relates to a method for producing an aromatic compound that is useful as a raw material for agrochemicals and highly functional materials.

2. Description of the Related Art

Aromatic amines and anilides are used as raw materials for agrochemicals and highly functional materials (see, for example, JP2004-307412A and JP2004-307413A). Regarding a synthesis method for an aromatic amine, a method of using cyclohexene as a starting raw material, and subjecting the same to reactions with acetic anhydride, and then acetyl chloride or hydrogen bromide, thereby performing hydrolysis (JP2009-514867A), a Semmler-Wolff reaction performed using a palladium catalyst (J. Am. Chem. Soc., 2013, 135, p. 13664-13667), and a Semmer-Wolff reaction performed using acetic anhydride and sodium iodide (JP2012-532186A; Org. Process Res. Dev., 2012, 16, p. 1746-1753; and Tetrahedron Letters, 2014, vol. 55, p. 3348-3350) are known.

SUMMARY OF THE INVENTION

The Semmler-Wolff reaction described in JP2012-532186A and the like has a problem that the yield is not always sufficient, and there is a need for improvement in order to industrially utilize the reaction.

Thus, the present invention provides a method for producing an aromatic compound, which allows a particular aromatic compound to be obtained at high yield and can be industrially utilized.

In the reactions of JP2012-532186A; Org. Process Res. Dev., 2012, 16, p. 1746-1753; and Tetrahedron Letters, 2014, vol. 55, p. 3348-3350, a two-step acylation of an oxime and an elimination reaction proceed, and it has been considered that as NaI is used, a highly active acylating agent (Ac-I) is produced, and second acylation is accelerated. Meanwhile, the inventors of the present invention found that by using a hydroquinone compound and a palladium compound as catalysts, the reaction is carried out efficiently, and the yield of the product is increased, thus completing the invention. Meanwhile, it is speculated that the hydroquinone compound and the palladium compound function as oxidation-reduction catalysts (redox catalysts).

That is, the invention provides a method for producing an aromatic compound, comprising an aromatization reaction which includes reacting an oxime compound represented by Formula (1):

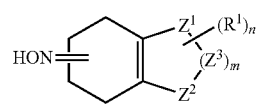

(in the formula, $R^1$ represents a halogen atom, a $C_{1-6}$ alkyl group, a $C_{3-8}$ cycloalkyl group, a $C_{1-6}$ alkoxy-$C_{1-6}$ alkyl group, an ar-$C_{1-6}$ alkyl group, a $C_{1-6}$ alkoxy group, an aryl group, or a heteroaryl group;

$Z^1$, $Z^2$, and $Z^3$ each independently represent a carbon atom, a nitrogen atom, or an oxygen atom, while the ring formed by $Z^1$, $Z^2$, and $Z^3$ is an aromatic ring;

n represents an integer from 0 to 3;

in a case where n is 2 or greater, a plurality of $R^1$'s existing therein may be identical with or different from each other;

m represents an integer of 1 or 2; and in a case where m is 2, a plurality of $Z^3$'s existing therein may be identical with or different from each other)

with an acylating agent in the presence of a hydroquinone compound and a palladium compound, and thus obtaining an aromatic compound represented by Formula (2):

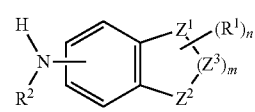

(in the formula, $R^1$, $Z^1$, $Z^2$, $Z^3$, n, and m respectively have the same meanings as described above; and $R^2$ represents an acyl group).

The acylating agent is preferably a carboxylic acid anhydride or a carboxylic acid halide, and is more preferably acetic anhydride.

The amount of use of the acylating agent is preferably 1 to 10 times the molar amount of the oxime compound.

The hydroquinone compound is preferably a hydroquinone compound having a $C_{1-12}$ alkyl group, and is more preferably a hydroquinone compound having a $C_{4-12}$ alkyl group containing a quaternary carbon atom.

The hydroquinone compound is preferably 2,5-bis(1,1,3,3-tetramethylbutyl)hydroquinone, 2,5-di-t-amylhydroquinone, or 2,5-di-t-butylhydroquinone, and is more preferably 2,5-di-t-butylhydroquinone.

The palladium compound is preferably $Pd(OAc)_2$, $Pd_2(dba)_3$, $Pd(acac)_2$, or Pd/C, and is more preferably $Pd(OAc)_2$.

The ratio of the amounts of use of the palladium compound and the hydroquinone compound is preferably 1:1 to 1:50 as a molar ratio.

The reaction solvent for the aromatization reaction is preferably an aromatic hydrocarbon, and is more preferably toluene, xylene, or ethylbenzene.

It is preferable that the oxime compound represented by Formula (1) is an oxime compound represented by Formula (3):

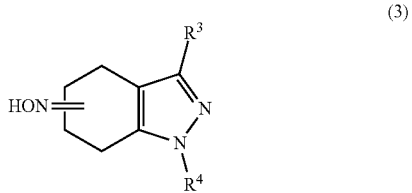

(3)

(in the formula, $R^3$ and $R^4$ each independently represent a hydrogen atom, a halogen atom, a $C_{1-6}$ alkyl group, a $C_{3-8}$ cycloalkyl group, a $C_{1-6}$ alkoxy-$C_{1-6}$ alkyl group, an ar-$C_{1-6}$ alkyl group, a $C_{1-6}$ alkoxy group, an aryl group, or a heteroaryl group); and the aromatic compound represented by Formula (2) is an aromatic compound represented by Formula (4):

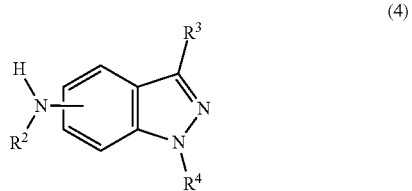

(4)

(in the formula, $R^3$ and $R^4$ respectively have the same meanings as described above; and $R^2$ represents an acyl group).

The production method of the invention can produce a particular aromatic compound at high yield and is therefore suitable for industrial production of aromatic compounds. Furthermore, the aromatic compound obtainable by the production method of the invention is useful as a raw material for agrochemicals and highly functional materials.

DESCRIPTION OF THE PREFERRED EMBODIMENTS

The present invention will be described in detail below.

In the invention, unless particularly stated otherwise, % means % by mass.

In the invention, unless particularly stated otherwise, the various terms have the following meanings.

A halogen atom means a fluorine atom, a chlorine atom, a bromine atom, or an iodine atom.

The $C_{1-6}$ alkyl group means a linear or branched $C_{1-6}$ alkyl group such as a methyl, ethyl, propyl, isopropyl, butyl, sec-butyl, isobutyl, tert-butyl, pentyl, isopentyl, 2-methylbutyl, 2-pentyl, 3-pentyl, or hexyl group.

The $C_{3-8}$ cycloalkyl group means a $C_{3-8}$ cycloalkyl group such as a cyclopropyl, cyclobutyl, cyclopentyl, or cyclohexyl group.

The $C_{1-6}$ alkoxy-$C_{1-6}$ alkyl group means a $C_{1-6}$ alkyloxy-$C_{1-6}$ alkyl group such as a methoxymethyl, methoxyethyl, or 1-ethoxyethyl group.

The ar-$C_{1-6}$ alkyl group means an ar-$C_{1-6}$ alkyl group (aryl-$C_{1-6}$ alkyl group) such as a benzyl, diphenylmethyl, trityl, phenethyl, 2-phenylpropyl, 3-phenylpropyl, or naphthylmethyl group.

The $C_{1-6}$ alkoxy group means a linear or branched $C_{1-6}$ alkyloxy group such as a methoxy, ethoxy, propoxy, isopropoxy, butoxy, isobutoxy, sec-butoxy, tert-butoxy, pentyloxy, or hexyloxy group.

The aryl group means a phenyl or naphthyl group.

The heteroaryl group means an aryl group having a heteroatom, such as a pyridyl group, a pyrazyl group, a pyrimidyl group, a pyridazyl group, a pyrrole group, a pyrazolyl group, an imidazolyl group, a triazolyl group, a benzoxazolyl group, a benzothiazolyl group, or a quinolyl group.

The acyl group means a formyl group, a $C_{2-6}$ alkanoyl group, an aroyl group, or a heterocyclic carbonyl group. The $C_{2-6}$ alkanoyl group means a linear or branched $C_{2-6}$ alkanoyl group such as an acetyl, propionyl, valeryl, isovaleryl, or pivaloyl group.

The $C_{4-12}$ alkyl group containing a quaternary carbon atom means a $C_{4-12}$ alkyl group containing a quaternary carbon atom, such as 1,1,3,3-tetramethylbutyl, t-amyl that is bonded to a carbon atom, or t-butyl that is bonded to a carbon atom.

The $C_{1-12}$ alkyl group means a linear or branched $C_{1-6}$ alkyl group, such as an n-heptyl group, an n-octyl group, an n-nonyl group, an n-decanyl group, an n-undecanyl group, or an n-dodecanyl group, in addition to the $C_{1-6}$ alkyl group and the $C_{4-12}$ alkyl group containing a quaternary carbon atom.

Next, the production method of the invention will be explained.

The production method of the invention includes an aromatization reaction which includes reacting an oxime compound represented by Formula (1):

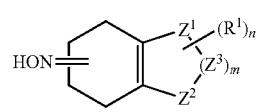

(1)

(in the formula, $R^1$ represents a halogen atom, a $C_{1-6}$ alkyl group, a $C_{3-8}$ cycloalkyl group, a $C_{1-6}$ alkoxy-$C_{1-6}$ alkyl group, an ar-$C_{1-6}$ alkyl group, a $C_{1-6}$ alkoxy group, an aryl group, or a heteroaryl group;

$Z^1$, $Z^2$, and $Z^3$ each independently represent a carbon atom, a nitrogen atom, or an oxygen atom, while the ring formed by $Z^1$, $Z^2$, and $Z^3$ is an aromatic ring;

n represents an integer from 0 to 3;

in a case where n is 2 or greater, a plurality of $R^1$'s existing therein may be identical with or different from each other;

m represents an integer of 1 or 2; and in a case where m is 2, a plurality of $Z^3$'s existing therein may be identical with or different from each other)

with an acylating agent in the presence of a hydroquinone compound and a palladium compound, and thus obtaining an aromatic compound represented by Formula (2):

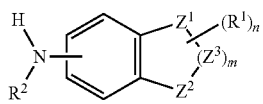

(2)

(in the formula, $R^1$, $Z^1$, $Z^2$, $Z^3$, n, and m respectively have the same meanings as described above; and $R^2$ represents an acyl group).

The inventors of the present invention speculate that as the hydroquinone compound and the palladium compound function as redox catalysts, the aromatization reaction proceeds smoothly, and high yield is obtained.

The hydroquinone compound is a compound having a structure in which two hydroxyl groups are bonded to a benzene ring, and the hydroquinone compound may have a substituent. A hydroquinone compound having a $C_{1-12}$ alkyl group is preferred. The number of $C_{1-12}$ alkyl groups carried by the hydroquinone compound is an integer from 1 to 4, preferably an integer from 1 to 3, more preferably an integer of 1 or 2, and even more preferably an integer of 2.

Examples of the hydroquinone compound having a $C_{1-12}$ alkyl group include a hydroquinone compound having a $C_{1-2}$ alkyl group, and a hydroquinone compound having a $C_{4-12}$ alkyl group containing a quaternary carbon atom; however, a hydroquinone compound having a $C_{4-12}$ alkyl group containing a quaternary carbon atom is preferred. The $C_{4-12}$ alkyl group containing a quaternary carbon atom is preferably a $C_{3-8}$ alkyl group containing a quaternary carbon atom, and is more preferably 1,1,3,3-tetramethylbutyl, a t-amyl group, or a t-butyl group.

Such a hydroquinone compound is preferably 2,5-bis(1,1,3,3-tetramethylbutyl)hydroquinone, 2,5-di-t-amylhydroquinone, or 2,5-di-t-butylhydroquinone, and 2,5-di-t-butylhydroquinone is particularly preferred.

In a case in which the hydroquinone compound has a $C_{4-12}$ alkyl group containing a quaternary carbon atom, by-products produced by a reaction between the oxime compound as a starting raw material and the hydroquinone compound can be suppressed, and by using the hydroquinone compound in combination with the palladium compound according to the invention, further enhancement of yield and productivity can be promoted.

Here, the hydroquinone compound having a $C_{1-2}$ alkyl group may be a hydroquinone compound having a methyl group. The number of methyl groups carried by the hydroquinone compound is an integer from 1 to 4, preferably an integer from 1 to 3, and more preferably an integer of 2. Examples of the hydroquinone compound having a $C_{1-2}$ alkyl group include methylhydroquinone, 2,6-dimethylhydroquinone, 2,5-dimethylhydroquinone, 2,3-dimethylhydroquinone, and trimethylhydroquinone. However, 2,6-dimethylhydroquinone, 2,5-dimethylhydroquinone, and 2,3-dimethylhydroquinone are preferred, and 2,6-dimethylhydroquinone is particularly preferred.

The amount of use of the hydroquinone compound is preferably 0.1 mol % to 50 mol %, more preferably 1 mol % to 40 mol %, and even more preferably 10 mol % to 30 mol %, with respect to the oxime compound as a starting raw material.

The palladium compound is not particularly limited as long as the palladium compound functions as a redox catalyst, and any known palladium compound can be used. $Pd(OAc)_2$ (palladium(II) acetate), $Pd_2(dba)_3$ (tris(dibenzylideneacetone)dipalladium(0)), $Pd(acac)_2$ (bis(2,4-pentanedionato)palladium(II)), or Pd/C (palladium carbon) is preferred, and $Pd(OAc)_2$ is particularly preferred.

The amount of use of the palladium compound is preferably 0.01 mol % to 20 mol %, more preferably 0.01 mol % to 10 mol %, and even more preferably 0.01 mol % to 5 mol %, with respect to the oxime compound as a starting raw material. In this invention, by using the palladium compound in combination with a hydroquinone compound, the aromatization reaction can be carried out with a smaller amount of use of the palladium compound, and cost reduction in industrial production can be promoted.

The ratio of the amounts of use of the palladium compound and the hydroquinone compound is preferably 1:1 to 1:50, and more preferably 1:5 to 1:30, as a molar ratio. In a case where such a ratio of the amounts of use is satisfied, the oxidation-reduction reaction in the reaction is optimized, this contributes to an increase in the yield, and the amount of use of the palladium compound can be reduced. Therefore, cost reduction in industrial production can be promoted.

Regarding a combination of the palladium compound and the hydroquinone compound, a combination of $Pd(OAc)_2$ and a hydroquinone compound having a $C_{4-12}$ alkyl group containing a quaternary carbon atom is preferred, and a combination of 2,5-di-t-butylhydroquinone and $Pd(OAc)_2$ is particularly preferred. In regard to the oxidation-reduction reaction, if any of oxidation and reduction is too strong, the reaction does not proceed smoothly; however, the present inventors speculate that in a case where such a combination is employed, a balance is achieved between oxidation and reduction, and the reaction proceeds efficiently.

Next, the oxime compound represented by Formula (1) and the aromatic compound represented by Formula (2) described above will be explained.

In regard to the oxime compound represented by Formula (1), $R^1$ is preferably a halogen atom, a $C_{1-6}$ alkyl group, a $C_{3-8}$ cycloalkyl group, a $C_{1-6}$ alkoxy-$C_{1-6}$ alkyl group, an ar-$C_{1-6}$ alkyl group, or a $C_{1-6}$ alkoxy group; and is particularly preferably a $C_{1-6}$ alkoxy-$C_{1-6}$ alkyl group or an ar-$C_{1-6}$ alkyl group. Regarding the $C_{1-6}$ alkoxy-$C_{1-6}$ alkyl group, a $C_{1-3}$ alkoxy-$C_{1-3}$ alkyl group is preferred, and a methoxyethyl group is particularly preferred. Regarding the ar-$C_{1-6}$ alkyl group, an ar-$C_{1-3}$ alkyl group is preferred, and a benzyl group is particularly preferred.

$Z^1$, $Z^2$, and $Z^3$ mentioned above are each independently preferably a carbon atom or a nitrogen atom.

n is preferably an integer from 1 to 3, and more preferably 1.

m is preferably 1.

In regard to the aromatic compound represented by Formula (2) thus obtainable, suitable ranges of $R^1$, $Z^1$, $Z^2$, $Z^3$, n, and m are the same as those of the oxime compound represented by Formula (1). Furthermore, $R^2$ is preferably a $C_{2-6}$ alkanoyl group, and is particularly preferably an acetyl group.

In regard to the production method of the invention, even in a case where the aromatic compound represented by Formula (2) is an indazole, a benzimidazole, an indole, an isoindole, a quinoline, an isoquinoline, a quinoxaline, a quinazoline, a benzofuran, or an isobenzofuran, the production method is useful because these aromatic compounds can be synthesized efficiently. Among these aromatic compounds, the production method is suitable for the production of an indazole, a benzimidazole, an indole, or an isoindole.

In regard to the production method of the invention, it is preferable that the oxime compound represented by Formula (1) is an oxime compound represented by Formula (3):

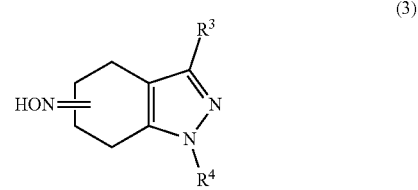

(in the formula, $R^3$ and $R^4$ each independently represent a hydrogen atom, a halogen atom, a $C_{1-6}$ alkyl group, a $C_{3-8}$ cycloalkyl group, a $C_{1-6}$ alkoxy-$C_{1-6}$ alkyl group, an ar-$C_{1-6}$ alkyl group, a $C_{1-6}$ alkoxy group, an aryl group, or a heteroaryl group); and the aromatic compound represented by Formula (2) is an aromatic compound represented by Formula (4):

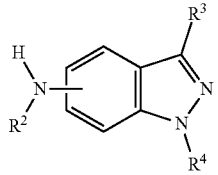

(4)

(in the formula, $R^3$ and $R^4$ respectively have the same meanings as described above; and $R^2$ represents an acyl group).

In regard to the oxime compound represented by Formula (3), $R^3$ is preferably a hydrogen atom. $R^4$ is preferably a halogen atom, a $C_{1-6}$ alkyl group, a $C_{3-8}$ cycloalkyl group, a $C_{1-6}$ alkoxy-$C_{1-6}$ alkyl group, an ar-$C_{1-6}$ alkyl group, or a $C_{1-6}$ alkoxy group; and is particularly preferably a $C_{1-6}$ alkoxy-$C_{1-6}$ alkyl group or an ar-$C_{1-6}$ alkyl group. The $C_{1-6}$ alkoxy-$C_{1-6}$ alkyl group is preferably a $C_{1-3}$ alkoxy-$C_{1-3}$ alkyl group, and is particularly preferably a methoxyethyl group. The ar-$C_{1-6}$ alkyl group is preferably an ar-$C_{1-3}$ alkyl group, and is particularly preferably a benzyl group.

In the aromatic compound represented by Formula (4) thus obtainable, suitable ranges of $R^3$ and $R^4$ are the same as those of the oxime compound represented by Formula (3). Furthermore, $R^2$ is preferably a $C_{2-6}$ alkanoyl group, and is particularly preferably an acetyl group.

Furthermore, it is preferable that the oxime compound represented by Formula (3) is an oxime compound represented by Formula (5):

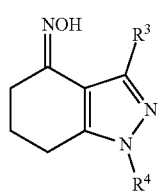

(5)

and the aromatic compound represented by Formula (4) is an aromatic compound represented by Formula (6):

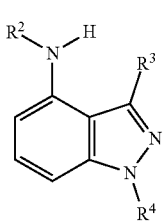

(6)

In the formulae described above, $R^3$ and $R^4$ respectively have the same meanings as described above, and $R^2$ represents an acyl group. Suitable ranges thereof are similar to those of the oxime compound represented by Formula (3) and the aromatic compound represented by Formula (4).

Furthermore, it is preferable that the oxime compound represented by Formula (3) is an oxime compound represented by Formula (7):

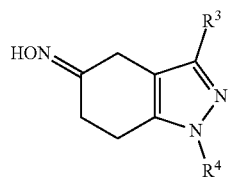

(7)

and the aromatic compound represented by Formula (4) is an aromatic compound represented by Formula (8):

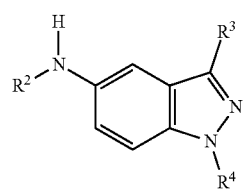

(8)

In the formulae described above, $R^3$ and $R^4$ respectively have the same meanings as described above, and $R^2$ represents an acyl group. Suitable ranges thereof are similar to those of the oxime compound represented by Formula (3) and the aromatic compound represented by Formula (4).

Next, the acylating agent described above will be explained.

The acylating agent is preferably a carboxylic acid anhydride or a carboxylic acid halide. Examples of the acylating agent include acetic anhydride, acetyl chloride, trifluoroacetic anhydride, chloroacetic anhydride, chloroacetyl chloride, dichloroacetic anhydride, and trichloroacetic anhydride, and acetic anhydride is particularly preferred. The amount of use of the acylating agent is 1 to 10 times, preferably 1 to 5 times, and more preferably 1.5 to 4 times, the molar amount of the oxime compound.

In the following description, other conditions for the aromatization reaction will be explained.

The solvent for the aromatization reaction is not particularly limited as long as the solvent does not affect the reaction. Examples of the solvent include aromatic hydrocarbons, and toluene, xylene, or ethylbenzene is preferred. These solvents may be used singly or as mixtures.

The amount of use of the solvent is not particularly limited; however, the amount of use may be 1 to 500 times the amount (v/w) of the oxime compound.

The aromatization reaction is performed by stirring a reaction mixture at an adequate temperature (for example, 0° C. to 200° C.) for a certain time period (for example, for 10 minutes to 12 hours). The reaction temperature is preferably 50° C. to 150° C., more preferably 90° C. to 140° C., and even more preferably 110° C. to 130° C. The reaction time is preferably for 10 minutes to 7 hours, more preferably 10 minutes to 5 hours and even more preferably 30 minutes to 3 hours.

According to the invention, the aromatization reaction proceeds at low temperature for a short time period, and the target product is obtained at high yield. Therefore, the production method is suitable for industrial production.

The aromatic compound represented by Formula (2), (4), (6), or (8) thus obtained may be further converted to a salt by reacting the aromatic compound with a mineral acid such as hydrochloric acid, hydrogen bromide, or sulfuric acid.

Next, a method for producing the oxime compound as a production raw material will be explained.

The oxime compound can be synthesized based on the methods described in known literatures, and for example, the oxime compound can be synthesized by the method described in Tetrahedron Lett., 2014, 55, 3348-3350.

Among the oxime compounds represented by Formula (5), an oxime compound in which $R^3$ represents a hydrogen atom can be produced by, for example, the following reaction by using cyclohexane-1,3-dione as a starting material.

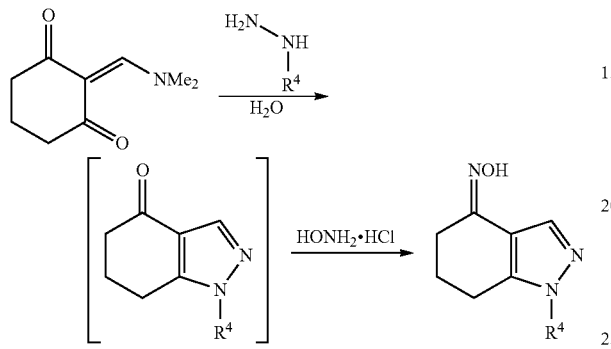

In the formulae, $R^4$ has the same meaning as described above, while a suitable range thereof is similar to that described above; and Me represents a methyl group.

EXAMPLES

Hereinafter, the invention will be described by way of Examples, Comparative Examples, and Reference Examples; however, the invention is not intended to be limited to these.

For medium-pressure preparative column chromatography, Smart FLASH EPCLC-W-Prep 2XY (Yamazen Corporation) was used.

The mixing ratio for the eluent is a volume ratio. For example, the description "ethyl acetate/hexane=1:1→ethyl acetate/hexane 4:1" implies that an eluent of 50 mass % ethyl acetate/50 mass % hexane is changed finally to an eluent of 80 mass % ethyl acetate/20 mass % hexane.

The $^1$H-NMR spectra were measured using tetramethylsilane as an internal standard and using Bruker AV400N (Bruker Corporation), and all of the δ values are expressed in ppm.

In an ultra performance liquid chromatography-mass spectrometry, measurement was performed using AQUITY UPLC H-Class System (Waters Corporation). Hereinafter, this will be abbreviated to UPLC-MS.

Various abbreviations used in various Examples have the following meanings.
Me: Methyl
Ac: Acetyl
Ph: Phenyl
Bn: Benzyl

Reference Example 1

1-Benzyl-6,7-dihydro-1H-indazol-4(5H)-one oxime was obtained by the reaction described below, by referring to Tetrahedron Lett., 2014, 55, 3348-3350. The results of $^1$H-NMR are presented below.

$^1$H-NMR (CDCl$_3$) δ value: A $^1$H-NMR analysis was performed, and as a result, the ratio of E-form/Z-form was 70:30.

$^1$H-NMR (CDCl$_3$) δ value:

1.88-2.06 (2H, m), 2.44-2.50 (1.4H, m), 2.59 (0.6H, t, J=6.01 Hz), 2.63 (1.4H, t, J=6.0 Hz), 2.71 (0.6H, t, J=6.0 Hz), 5.28 (0.6H, s), 5.31 (1.4H, s), 7.12 (2H, d, J=8.0 Hz), 7.25-7.36 (3H, m), 7.69 (1H, s), 7.78 (0.3H, s), 8.27 (0.7H, s)

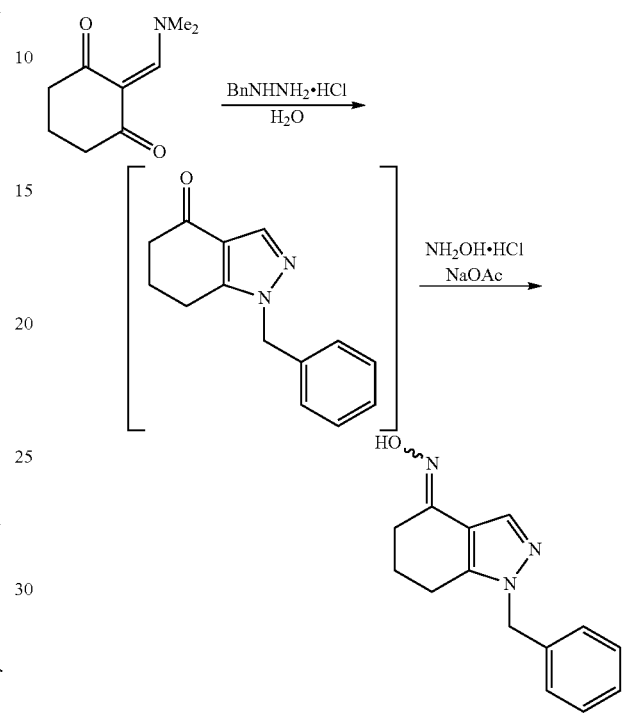

Example 1 (Pd(OAc)$_2$-DTBHQ Method)

241 mg of 1-benzyl-6,7-dihydro-1H-indazol-4(5H)-one oxime obtained in Reference Example 1, 2 mL of xylene, 4.4 mg of palladium acetate, 44 mg of 2,5-di-tert-butylhydroquinone, and 189 µL of acetic anhydride were mixed, and the mixture was stirred for 2 hours at 120° C. After being cooled to room temperature, the reaction liquid was purified by medium-pressure preparative column chromatography (eluent ethyl acetate/hexane=1:1→ethyl acetate/hexane 4:1), and 150 mg of N-(1-benzyl-1H-indazol-4-yl)acetamide, which was a colorless oily substance, was obtained in the following scheme. The yield of the product was 57%. The $^1$H-NMR data of the product are shown below.

$^1$H-NMR (CDCl$_3$) δ value:

2.22 (3H, s), 5.53 (2H, s), 7.06-7.37 (7H, m), 7.66 (1H, d, J=7.6 Hz), 8.00 (s, 1H), 8.08 (s, 1H)

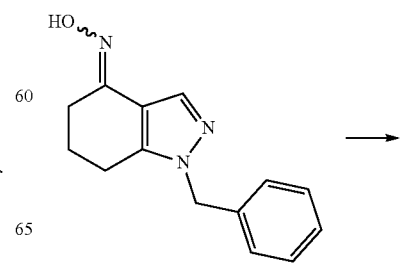

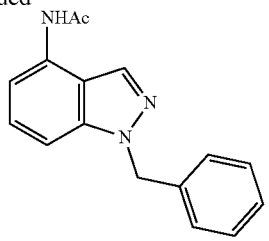

Example 2 (Pd(OAc)₂-DMHQ Method)

241 mg of 1-benzyl-6,7-dihydro-1H-indazol-4(5H)-one oxime obtained in Reference Example 1, 2 mL of xylene, 4.4 mg of palladium acetate, 27.6 mg of 2,6-dimethylhydroquinone, and 189 μL of acetic anhydride were mixed, and the mixture was stirred for 2 hours at 120° C. The reaction mixture was analyzed by UPLC-MS, and production of N-(1-benzyl-1H-indazol-4-yl)acetamide was confirmed. The production ratio based on a comparison with the internal standard (4-ethylbiphenyl) was 45%.

Example 3 (Pd₂Dba₃-DTBHQ Method)

241 mg of 1-benzyl-6,7-dihydro-1H-indazol-4(5H)-one oxime obtained in Reference Example 1 was mixed with 2 mL of xylene, 10 mg of tris(dibenzylideneacetone)dipalladium-chloroform complex, 44 mg of 2,5-di-tert-butylhydroquinone, and 189 μL of acetic anhydride, and the mixture was stirred for 2 hours at 120° C. The reaction mixture was analyzed by UPLC-MS, and production of N-(1-benzyl-1H-indazol-4-yl)acetamide was confirmed. The production ratio based on a comparison with the internal standard (4-ethylbiphenyl) was 54%.

Example 4 (Pd(OAc)₂-2,5-Di-tAmHQ Method)

241 mg of 1-benzyl-6,7-dihydro-1H-indazol-4(5H)-one oxime obtained in Reference Example 1 was mixed with 2 mL of xylene, 4.4 mg of palladium acetate, 50.1 mg of 2,5-di-tert-amylhydroquinone, and 189 μL of acetic anhydride, and the mixture was stirred for 2 hours at 120° C. The reaction mixture was analyzed by UPLC-MS, and production of N-(1-benzyl-1H-indazol-4-yl)acetamide was confirmed. The production ratio based on a comparison with the internal standard (4-ethylbiphenyl) was 58%.

Example 5 (Pd(OAc)₂-2,5-Bis(1,1,3,3-Tetramethylbutyl)HQ Method)

241 mg of 1-benzyl-6,7-dihydro-1H-indazol-4(5H)-one oxime obtained in Reference Example 1 was mixed with 2 mL of xylene, 4.4 mg of palladium acetate, 66.9 mg of 2,5-bis(1,1,3,3-tetramethylbutyl)hydroquinone, and 189 μL of acetic anhydride, and the mixture was stirred for 2 hours at 120° C. The reaction mixture was analyzed by UPLC-MS, and production of N-(1-benzyl-1H-indazol-4-yl)acetamide was confirmed. The production ratio based on a comparison with the internal standard (4-ethylbiphenyl) was 51%.

Comparative Example 1

A reaction similar to that of Example 1 was performed, except that the palladium acetate and 2,5-di-tert-butylhydroquinone used in Example 1 were not used. The reaction mixture was analyzed by UPLC-MS, and production of N-(1-benzyl-1H-indazol-4-yl)acetamide was confirmed. The production ratio based on a comparison with the internal standard (4-ethylbiphenyl) was 1%.

Comparative Example 2

A reaction similar to that of Example 1 was performed, except that the palladium acetate and 2,5-di-tert-butylhydroquinone used in Example 1 were not used, and 75 mg of sodium iodide was used. The reaction mixture was analyzed by UPLC-MS, and production of N-(1-benzyl-1H-indazol-4-yl)acetamide was confirmed. The production ratio based on a comparison with the internal standard (4-ethylbiphenyl) was 24%.

Comparative Example 3

A reaction similar to that of Example 1 was performed, except that the palladium acetate used in Example 1 was not used. The reaction mixture was analyzed by UPLC-MS, and production of N-(1-benzyl-1H-indazol-4-yl)acetamide was confirmed. The production ratio based on a comparison with the internal standard (4-ethylbiphenyl) was 9%.

Example 6

Production was carried out in the same manner as in Example 1, except that 1-benzyl-6,7-dihydro-1H-indazol-5(4H)-one oxime was used as the oxime compound. Thus, N-(1-benzyl-1H-indazol-5-yl)acetamide, which was a colorless oily substance, was obtained in the following scheme. The yield of the product was 43%. The ¹H-NMR data of the product are shown below.

¹H-NMR (CDCl₃) δ value:

2.19 (3H, s), 5.57 (2H, s), 7.15 (1H, s), 7.17 (1H, d, J=1.2 Hz), 7.24-7.34 (5H, m), 7.35 (1H, s), 7.97 (1H, d, J=1.2 Hz), 7.99 (1H, s)

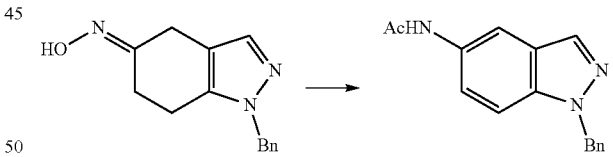

Example 7

Production was carried out in the same manner as in Example 1, except that 1-t-butyl-6,7-dihydro-1H-indazol-4(5H)-one oxime was used as the oxime compound. Thus, N-(1-(t-butyl)-1H-indazol-4-yl)acetamide, which was a colorless oily substance, was obtained in the following scheme. The yield of the product was 52%. The ¹H-NMR data of the product are shown below.

¹H-NMR (CDCl₃) δ value:

1.77 (9H, s), 2.28 (3H, s), 7.28 (1H, t, J=6.0 Hz), 7.46 (1H, d, J=6.0 Hz), 7.67 (1H, s), 7.72 (1H, d, J=6.0 Hz), 7.95 (1H, s)

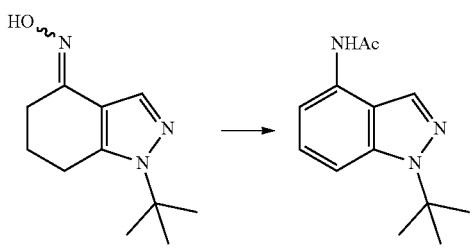 [SMILES: CC(C)(C)n1ncc2c1CCCC2=NO ; CC(=O)Nc1cccc2c1cnn2C(C)(C)C]

Example 8

Production was carried out in the same manner as in Example 1, except that 1-isopropyl-6,7-dihydro-1H-indazol-4(5H)-one oxime was used as the oxime compound. Thus, N-(1-isopropyl-1H-indazol-4-yl)acetamide, which was a colorless oily substance of the following reaction formula, was obtained. The yield of the product was 87%. The $^1$H-NMR data of the product are shown below.

$^1$H-NMR (CDCl$_3$) δ value:
1.59 (6H, d, J=6.8 Hz), 2.29 (3H, s), 4.83 (1H, m), 7.21 (1H, d, J=7.8 Hz), 7.33 (1H, t, J=7.8 Hz), 7.62 (1H, s), 7.71 (1H, d, J=7.8 Hz), 8.01 (1H, s)

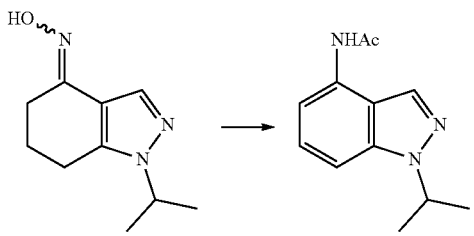 [SMILES: CC(C)n1ncc2c1CCCC2=NO ; CC(=O)Nc1cccc2c1cnn2C(C)C]

The production method of the invention can produce a particular aromatic compound at high yield, and the production method is useful for industrial production of aromatic compounds.

What is claimed is:

1. A method for producing an aromatic compound, comprising an aromatization reaction which includes reacting an oxime compound represented by Formula (1):

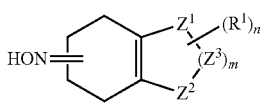

(in the formula, R$^1$ represents a halogen atom, a C$_{1-6}$ alkyl group, a C$_{3-8}$ cycloalkyl group, a C$_{1-6}$ alkoxy-C$_{1-6}$ alkyl group, an ar-C$_{1-6}$ alkyl group, a C$_{1-6}$ alkoxy group, an aryl group, or a heteroaryl group;

Z$^1$, Z$^2$, and Z$^3$ each independently represent a carbon atom, a nitrogen atom, or an oxygen atom, while the ring formed by Z$^1$, Z$^2$, and Z$^3$ is an aromatic ring;

n represents an integer from 0 to 3;

in a case where n is 2 or greater, a plurality of R$^1$'s existing therein may be identical with or different from each other;

m represents an integer of 1 or 2; and in a case where m is 2, a plurality of Z$^3$'s existing therein may be identical with or different from each other)

with an acylating agent in the presence of a hydroquinone compound and a palladium compound, and thus obtaining an aromatic compound represented by Formula (2):

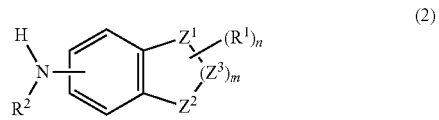

(in the formula, R$^1$, Z$^1$, Z$^2$, Z$^3$, n, and m respectively have the same meanings as described above; and R$^2$ represents an acyl group).

2. The method for producing an aromatic compound according to claim 1, wherein the acylating agent is a carboxylic acid anhydride or a carboxylic acid halide.

3. The method for producing an aromatic compound according to claim 2, wherein the acylating agent is acetic anhydride.

4. The method for producing an aromatic compound according to claim 1, wherein the amount of use of the acylating agent is 1 to 10 times the molar amount of the oxime compound.

5. The method for producing an aromatic compound according to claim 1, wherein the hydroquinone compound is a hydroquinone compound having a C$_{1-12}$ alkyl group.

6. The method for producing an aromatic compound according to claim 1, wherein the hydroquinone compound is a hydroquinone compound having a C$_{4-12}$ alkyl group containing a quaternary carbon atom.

7. The method for producing an aromatic compound according to claim 1, wherein the hydroquinone compound is 2,5-bis(1,1,3,3-tetramethylbutyl)hydroquinone, 2,5-di-t-amylhydroquinone, or 2,5-di-t-butylhydroquinone.

8. The method for producing an aromatic compound according to claim 1, wherein the hydroquinone compound is 2,5-di-t-butylhydroquinone.

9. The method for producing an aromatic compound according to claim 1, wherein the palladium compound is palladium(II) acetate, tris(dibenzylideneacetone)dipalladium(0), bis(2,4-pentanedionato)palladium(II), or palladium-carbon.

10. The method for producing an aromatic compound according to claim 1, wherein the palladium compound is palladium(II) acetate.

11. The method for producing an aromatic compound according to claim 1, wherein the ratio of the amounts of use of the palladium compound and the hydroquinone compound is 1:1 to 1:50 as a molar ratio.

12. The method for producing an aromatic compound according to claim 1, wherein the reaction solvent for the aromatization reaction is an aromatic hydrocarbon.

13. The method for producing an aromatic compound according to claim 12, wherein the aromatic hydrocarbon is toluene, xylene, or ethylbenzene.

14. The method for producing an aromatic compound according to claim 1, wherein the oxime compound represented by Formula (1) is an oxime compound represented by Formula (3):

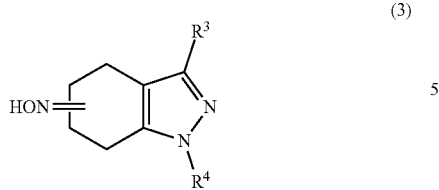

(3)

(in the formula, $R^3$ and $R^4$ each independently represent a hydrogen atom, a halogen atom, a $C_{1-6}$ alkyl group, a $C_{3-8}$ cycloalkyl group, a $C_{1-6}$ alkoxy-$C_{1-6}$ alkyl group, an ar-$C_{1-6}$ alkyl group, a $C_{1-6}$ alkoxy group, an aryl group, or a heteroaryl group); and the aromatic compound represented by Formula (2) is an aromatic compound represented by Formula (4):

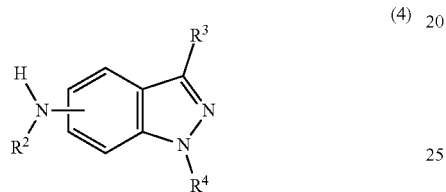

(4)

(in the formula, $R^3$ and $R^4$ respectively have the same meanings as described above; and $R^2$ represents an acyl group).

* * * * *